(12) United States Patent
Prakash

(10) Patent No.: US 6,939,567 B1
(45) Date of Patent: Sep. 6, 2005

(54) PHARMACEUTICAL AYURVEDIC PREPARATION

(75) Inventor: Vaidya Balendu Prakash, Dehradoon (IN)

(73) Assignees: National Research Development Corporation, Anusandhan Vikas, New Delhi (IN); Central Council for Research in Ayurveda and Siddha, New Delhi (IN)

( * ) Notice: Subject to any disclaimer, the term of this patent is extended or adjusted under 35 U.S.C. 154(b) by 0 days.

(21) Appl. No.: 10/070,540

(22) PCT Filed: Sep. 7, 1999

(86) PCT No.: PCT/IN99/00042

§ 371 (c)(1),
(2), (4) Date: May 24, 2002

(87) PCT Pub. No.: WO01/17540

PCT Pub. Date: Mar. 15, 2001

(51) Int. Cl.$^7$ .................. A61K 33/38; A61K 35/78
(52) U.S. Cl. .................. 424/618; 424/736; 424/773
(58) Field of Search ............... 424/618, 773, 424/776

(56) References Cited

U.S. PATENT DOCUMENTS 5,405,613 A * 4/1995 Rowland .................... 424/439
5,529,778 A * 6/1996 Rohatgi ..................... 424/725

OTHER PUBLICATIONS

Thakur et al., "The Ayurvedic medicines Haritaki, Amla and Bahira reduce cholesterol-induced atherosclerosis in rabbits," International Journay of Cardiology, vol. 21, No. 2, Nov. 1988, pp. 167-175.*
Smith et al "J. Ethon" vol. 47(2) pp 75-84 Jul. 7, 1995.*
http://www.sssbiotic.com/product/haritaki.asp Terminalia chebula [Harar] pp. 1-2*
http://botanical.com/site/column_poudhia/publish/journal. cgi?folder=journal&next=781 "Traditional medicinal . . . " p. 1.*
http://www.allayurveda.com/herbalcure3.htm "Herb That Cure" Kulthi p. 4.*
http://www.exoticnatural.com/appln.htm "Exotic Naturals" *Abelmoschus moschatus- Lata kasturi* p. 1.*
Dash, Vaidya Bhagwan, "Alchemy and Metallic Medicinces in Ayurveda." New Delhi: Concept Publishing Company, 1986, chapter 6, 7.
Smith, H.F. et al., "Ayurvedic herbal drugs with possible cytostatic activity", J. Ethnopharmacol, Jul. 7, 1995, pp. 75-84 (abstract).

* cited by examiner

*Primary Examiner*—Herbert J. Lilling
(74) *Attorney, Agent, or Firm*—VENABLE LLP

(57) ABSTRACT

The present invention relates to a process on ayurvedic preparation comprising in the steps of subjecting silver, mercury, sulphur and arsenic trisulphide to the steps of detoxification, grinding the detoxified mercury and silver in the presence of a citrus juice and then adding detoxified sulphur and again subjecting to the step of grinding to obtain a greyish black powder, adding detoxified arsenic trisulphide thereto and subjecting to the step of grinding, imparting a shape such as a ball thereto, coating the ball with detoxified sulphur in the presence of a citrus juice and subjecting the coated ball to the step of slow firing, adding detoxified arsenic trisulphide and firing, repeating said step of addition and firing ground in a citrus juice such that the weight of the ball is reduced by at least 10% to obtain an intermediate, adding serpentive and delphenium root thereto.

16 Claims, No Drawings

PHARMACEUTICAL AYURVEDIC PREPARATION

FIELD OF INVENTION

This invention relates to a pharmaceutical ayurvedic preparation for the treatment of leukemia. The preparation of the present invention has a particular application for the treatment of acute mycloid leukemia, acute promyelcocytic leukemia and acute lymphoblastic leukemia. The present invention also relates to a process for preparing the pharmaceutical ayurvedic preparation.

PRIOR ART

Chemical pharmaceutical preparations are normally prescribed for treatment of leukemia. No prior public literature is known for an ayurvedic preparation for treatment of leukemia.

OBJECTS OF THE INVENTION

An object of this invention is to propose a novel ayurvedic preparation for treatment of leukemia.

Another object of this invention is to propose an ayurvedic preparation for treatment of leukemia and which does not have any side effects.

DESCRIPTION OF THE INVENTION

According to this invention, there is provided a process for the preparation of an ayurvedic preparation comprising in the steps of subjecting silver, mercury, sulphur and arsenic trisulphide to the steps of detoxification, grinding the detoxified mercury and silver in the presence of a citrus juice and then adding detoxified sulphur and again subjecting to the step of grinding to obtain a greyish black powder, adding detoxified arsenic trisulphide thereto and subjecting to the step of grinding, imparting a shape such as a ball thereto, coating the ball with detoxified sulphur in the presence of a citrus juice and subjecting the coated ball to the step of slow firing, adding detoxified arsenic trisulphide and firing, repeating said steps of addition and firing ground in a citrus juice such that the weight of the ball is reduced by at least 10% to obtain an intermediate, adding serpentive and delphenium root thereto.

The expression detoxification used herein is not intended to imply that silver, mercury, sulphur and arsenic trisulphide are treated such as to detoxify the elements in the mixture stage, but to imply that such elements do not exhibit any adverse side effects in the end preparations.

In accordance with this invention, silver in a purified form which is subjected to a step of detoxification. Such a step of detoxification consists in converting silver bars into sheets and then to repetitive steps of heating and introduction into sesame oil. By way of example and without implying any limitation, such a step of heating and introducing into sesame oil is repeated several times, such as seven times.

Thereafter, the treated silver is again heated and then introduced into butter milk. The step of heating and introduction into butter milk after each step of heating is also repeated several times, such as seven times.

The partially detoxificated silver is again heated and then introduced into cow urine and which step is repeated several times, such as seven times.

The treated silver is again heated and introduced into a herbal composition. Such a step of heating and introduction into a herbal composition is again preferably repeated several times, such as seven times. The herbal composition comprises amla, harar and behera and present preferably in equal parts.

The treated silver is again heated several times and then after each step of heating is treated with kutli. Such a step is also repeated several times, such as seven times. The aforesaid step consits in the detoxification of silver. The process of the present invention includes the step of detoxification of mercury. For this purpose, an amalgam is first prepared from a mixture of copper, which may be in the form of wire, in lemon juice and mercury. Preferably ½–⅛ parts of copper wire is added to every one part of mercury which is then ground to obtain an amalgam. Such an amalgam is then subjected to a step of distillation to extract mercury therefrom. The step of grinding and distillation is effected several times in order to obtain detoxified mercury. Preferably but without implying any limitation to the step of detoxification is carried seven times.

The next step is the process consists in the purification of sulphur. For this purpose, crystalline sulphur is introduced into a crucible and having melted butter therein. Preferably, equal amounts of melted butter and sulphur are introduced into the crucible and heated on a low fire. Trifla is then added to the mixture and whereby a scum of pure sulphur is formed and removed.

The process also comprises in introducing arsenic trisulphide disposed within a cotton cloth and introduced into a vessel containing calcium oxide solution and then into another vessel of pumpkin juice or vice versa. The arsenic trisulphide is heated in calcium oxide solution and pumpkin juice for a period of 3 to 5 hours, such as 4 hours and, then dried.

The next step in the process consists in grinding detoxicated silver and mercury in the presence of citrus juice, such as lemon juice, and such that detoxicated silver is dissolved in mercury. Preferably, one part of detoxicated silver is added to one part of mercury and ground in the presence of lemon juice to form a powder. Thereafter, purified sulphur is added thereto and ground to greyish black powder. Preferably, one part of purified sulphur is added thereto. Upon grinding and obtaining a greyish black powder purified arsenic trisulphide is added to the greyish black powder in the presence of a citrus juice, such as lemon juice, which is then subjected to a step of grinding to obtain a paste. Such a paste is shaped into balls and then air dried. Preferably, one part of arsenic disulphide is added thereto.

The next step in the process consists in coating such balls with a paste of sulphur in lemon juice.

Such a ball is introduced into an earthenware vessel which is sealed with a strip of cotton and dipped in clay. The vessel is introduced into a bed containing dry cowdung which is then fired such that the temperature rises to a temperature of 500–600° C. and then gradually reduces.

The vessel is then opened and arsenic trisulphide is added thereto in the presence of lemon juice and subjected to the step of firing. The step of adding arsenic trisulphide and firing is repeated 30–60 time to obtain a more potent intermediate product, and such that the weight is reduced by at least 10%.

Such an intermediate product is thereafter added to serpentine and delphenium root and ground in distilled rose water for approximately seven days repeated with sandalwood water for seven day and finally with latakasturi water for seven days to obtain a paste which is then shaped into balls.

Further objects and advantages of this invention will be more apparent from the ensuing example and clinical trials.

EXMAPLE

Silver, mercury, sulphur and arsenic trisulphide was detoxified in a manner as described hereinabove.

Thereafter, the ball was prepared consisting of:
detoxified silver=250 gms
detoxified mercury=250 gms
detoxified sulphur=500 gms
detoxified arsenic trisulphide=250 gms The ball had a weight of 1250 gms and then provided with a coating of detoxified sulphur ground in lemon juice and such that the coated ball had a weight of 1400 gms. Such a ball was then introduced into an earthen vessel or pot and sealed with a strip of cotton, dipped in clay. The vessel is introduced into a pit containing cow dung and fired. Such a process was repeated as shown in Table 1 to product the intermediate product. Thereafter, the final product was prepared in a manner as described herein above.

TABLE 1

| VESSEL | GROUND ARSENIC trisulphide | WITH LEMON Juice | PERIOD DAYS | WT.BEFORE FIRING gm | PERIOD OF FIRING DAYS | WT. AFTER FIRING gm |
|---|---|---|---|---|---|---|
| 1 | 0 | 0 | 0 | 1400 | 1 | 940 |
| 1 | 25 g | 450 ml | 6 | 1120 | 1 | 975 |
| 1 | 25 g | 400 ml | 17 | 1100 | 1 | 940 |
| 1 | 25 g | 400 ml | 22 | 1050 | 1 | 940 |
| 2 | 25 g | 400 ml | 29 | 1110 | 1 | 930 |
| 2 | 25 g | 450 ml | 36 | 100 | 1 | 975 |
| 2 | 25 g | 400 ml | 41 | 1070 | 1 | 940 |
| 2 | 25 g | 400 ml | 50 | 1040 | 1 | 940 |
| 2 | 25 g | 450 ml | 58 | 1050 | 1 | 930 |
| 2 | 25 g | 550 ml | 67 | 1080 | 1 | 940 |
| 2 | 25 g | 500 ml | 73 | 1070 | 1 | 950 |
| 2 | 25 g | 750 ml | 80 | 1070 | 1 | 970 |
| 2 | 25 g | 750 ml | 84 | 1050 | 1 | 970 |
| 2 | 25 g | 800 ml | 89 | 1060 | 1 | 940 |
| 2 | 25 g | 900 ml | 96 | 1080 | 1 | 950 |
| 2 | 25 g | 900 ml | 103 | 1100 | 1 | 1000 |
| 2 | 25 g | 900 ml | 110 | 1120 | 1 | 970 |
| 2 | 25 g | 900 ml | 116 | 1050 | 1 | 950 |
| 2 | 25 g | 900 ml | 121 | 1020 | 1 | 950 |
| 2 | 25 g | 750 ml | 128 | 1050 | 1 | 990 |
| 2 | 25 g | 800 ml | 135 | 1080 | 1 | 980 |
| 2 | 25 g | 750 ml | 140 | 1050 | 1 | 950 |
| 2 | 25 g | 650 ml | 148 | 1050 | 1 | 950 |
| 2 | 25 g | 700 ml | 153 | 1020 | 1 | 950 |
| 2 | 25 g | 700 ml | 159 | 1080 | 1 | 980 |
| 2 | 25 g | 650 ml | 173 | 980 | 1 | 920 |

The results of clinical trials on patients with the preparation of the present invention were as follows:

TABLE 2

DETAILS OF THE PATIENTS WHO COMPLETED 90 DAYS OF TREATMENT FOR ACUTE PROMYELOCYTIC LEUKEMIA WITH PRESENT MEDICINE

| S.No. | Name/Age | Category Fresh/ Relapse | Duration of Treatment From | To | Status after 90 days |
|---|---|---|---|---|---|
| 1. | ARK/41 | F | Sep. 09, 1997 | Jan. 30, 1998 | Complete remission on Dec. 26, 1997 |
| 2. | VR/40 | F | Dec. 04, 1997 | Apr. 22, 1999 | Complete remission on Mar. 14, 1998 |
| 3. | PK/50 | F | Dec. 04, 1997 | Mar. 20, 1998 | Complete remission on Mar. 16, 1998 |
| 4. | VC/48 | R | Dec. 22, 1997 | Apr. 15, 1998 | complete remission on Apr. 01, 1998 |
| 5. | F/29 | R | Apr. 09, 1998 | Dec. 07, 1998 | Bone marrow not done, blood report normal |
| 6. | NS/15 | R | Apr. 18, 1998 | Jan. 30, 1999 | Complete remission on Jul. 25, 1998 |

TABLE 2-continued

DETAILS OF THE PATIENTS WHO COMPLETED 90 DAYS OF TREATMENT FOR ACUTE PROMYELOCYTIC LEUKEMIA WITH PRESENT MEDICINE

| S.No. | Name/Age | Category Fresh/ Relapse | Duration of Treatment From | To | Status after 90 days |
|---|---|---|---|---|---|
| 7. | PR/48 | F | Jan. 26, 1999 | May 15, 1999 | Complete remission on Apr. 12, 1999 |
| 8. | MS/28 | R | Feb. 19, 1999 | Jun. 15, 1999 | Complete remission on Jun. 11, 1999 |
| 9. | PS/29 | R | Mar. 25, 1999 | Jul. 05, 1999 | Complete remission on Jul. 03, 1999 |

F-Fresh, R-Relapse

TABLE 3

DETAILS OF BONE MARROW OF THE PATIENTS WHO COMPLETED 90 DAYS OF TREATMENT FOR ACUTE PROMYELOCYTIC LEUKEMIA

| S.No. | Name/Age | Before Ayurvedic treatment | After 90 days of Ayurvedic treatment |
|---|---|---|---|
| 1. | ARK/41 | BM no.5239863, replaced with abnormal promyelocytes-M3 | PS and BM no. 523986-D, is free of evidence of M3, normal hemopoitic cell |
| 2. | VR/40 | Bone marrow shows abnormal promyelocytes-M3 | Bone marrow in remission, no promyelocytic cells seen |
| 3. | PK/50 | Bone marrow replaced with abnormal promyelocytes-M3 | Bone marrow in remission with normal cells |
| 4. | VC/48 | Bone marrow shows hyper granulated M3 cells | Bone marrow in remission with normal hemopoitic cells |
| 5. | F/29 | Bone marrow shows abnormal promyelocytes-M3 | Bone marrow not done |
| 6. | NS/15 | Bone marrow shows 60–65% abnormal promyleocytes, APML relapse, $N_{8-10}$, $L_{3-5}$, MRBC 25% | Bone marrow in remission, no APML cells identified, PS shows $P_{64}L_{33}E_2M_1$ |
| 7. | PR/48 | Bone marrow shows hyper granulated promyleocytes AML-M3 | Bone marrow shows normal hemopoitic with mild megaloblastic change. There is no morphological evidence of residual leukemia |
| 8. | MS/28 | Bone marrow in relapse- AML-M3 | Bone marrow shows normal hemopoitic. No leukemic cells identified |
| 9. | PS/29 | Bone marrow shows total replacement by abnormal hyper granular promyleocytes | Bone marrow shows normal hemopoitic cells of all series. No evidence of leukemia seen |
| 10. | MN/30 | Bone marrow shows abnormal promyleocytes along with few normal neutrophils- AML-M3 relapse | Bone marrow shows normal hemopoitic cells in all series. No evidence of residual leukemia |

TABLE

DETAILS OF BLOOD REPORT OF TREATED APML CASES

| S. No. | Name/Age | Blood report | First day | After 30 days | After 60 days | After 90 days |
|---|---|---|---|---|---|---|
| 1. | ARK/41 | Hb gm % | 7.1 | 9.9 | 13.5 | 14.8 |
|  |  | TLC | 1100 | 1450 | 5100 | 3100 |
|  |  | DLC | $N_{10}L_{30}Abn_{60}$ | $N_{31}L_{69}$ | $N_{60}L_{34}E_6$ | $N_{57}L_{27}E_{10}M_4$ |
|  |  | ESR | 138 | 37 | 8 | — |
|  |  | Platelets | 19000 | 258000 | 172000 | 174000 |
| 2. | VR/40 | Hb gm % | 5.6 | 8.2 | 9.6 | 10.0 |
|  |  | TLC | 1600 | 620 | 3200 | 3900 |

TABLE-continued

DETAILS OF BLOOD REPORT OF TREATED APML CASES

| S. No. | Name/Age | Blood report | First day | After 30 days | After 60 days | After 90 days |
|---|---|---|---|---|---|---|
| | | DLC | $N_{35}L_{29}E_2M_2Abn_{30}$ | $N_{32}L_{22}E_4M_2Abno_{20}$ | $N_{40}L_{38}E_4Abn_{18}$ | $N_{73}L_{21}E_4M_2$ |
| | | ESR | — | — | — | |
| | | Platelets | 40000 | 180000 | 200000 | 200000 |
| 3. | PK/50 | Hb gm % | 10.2 | 9.3 | 10.1 | 13.9 |
| | | TLC | 2000 | 6800 | 7000 | 9000 |
| | | DLC | $N_7L_{10}M_2Abn_{81}$ | $N_{70}L_{30}$ | $N_{66}L_{33}E_1$ | $N_{63}L_{37}$ |
| | | ESR | — | — | 10 | — |
| | | Plateltes | 35000 | 25000 | 252000 | 330000 |
| 4. | VC/48 | Hb gm % | 8.0 | 9.5 | 11.8 | 9.6 |
| | | TLC | 28000 | 650 | 7500 | 4800 |
| | | DLC | $N_{30}L_{35}E_5M_4Abn_{26}$ | $N_{20}L_{80}$ | $N_{58}L_{26}M_2Abn_{14}$ | $N_{79}L_{13}Abn_4$ |
| | | ESR | 75 | — | — | — |
| | | Platelets | 110000 | 22000 | 85000 | 120000 |
| 5. | F/29 | Hb gm % | 9.0 | 9.0 | 5.0 | 9.6 |
| | | TLC | 4900 | 4900 | 2500 | 1000 |
| | | DLC | $N_8L_{47}M_5Abn_{40}$ | $N_8L_{45}M_5Abn_{40}$ | $N_{45}L_{54}B_1$ | $N_{26}L_5E_1Abn_{46}$ |
| | | ESR | — | — | 90 | 130 |
| | | Platelets | 75000 | 75000 | 18000 | 55000 |
| 6. | NS/15 | Hb gm % | 12.9 | 8.4 | 11.0 | 11.7 |
| | | TLC | 400 | 63200 | 7900 | 8500 |
| | | DLC | $N_{64}L_{36}$ | $N_5L_{10}Abn_{85}$ | $N_{57}L_{40}E_3$ | $N_{60}L_{37}E_3$ |
| | | ESR | — | 42 | 5 | 5 |
| | | Platelets | 130000 | 64000 | 238000 | 218000 |
| 7. | PR/48 | Hb gm % | 12.7 | 10.2 | 10.5 | 11.4 |
| | | TLC | 2000 | 3000 | 3500 | 5500 |
| | | DLC | $N_7L_{43}Abn_{50}$ | $N_{13}L_{27}E_4Abn_{56}$ | $N_{48}L_{37}E_6Abn_2B_1$ | $N_{55}L_{41}B_1Abn_2$ |
| | | ESR | 43 | — | — | — |
| | | Platelets | 76000 | 90000 | 298000 | 310000 |
| 8. | MS/28 | Hb gm % | 7.0 | 10.5 | 13.0 | 14.3 |
| | | TLC | 12200 | 5700 | 7200 | 9200 |
| | | DLC | $N_8L_{30}Abn_{62}$ | $N_{55}L_{44}E_1M_2$ | $N_{73}L_{22}E_5$ | $N_{64}L_{33}E_3$ |
| | | ESR | 48 | 5 | — | — |
| | | Platelets | 36000 | 103000 | 141000 | 169000 |
| 9. | PS/29 | Hb gm % | 8.4 | 12.2 | 15.0 | 14.9 |
| | | TLC | 2240 | 2900 | 5200 | 4600 |
| | | DLC | $N_{15}L_{10}M_5Abn_{70}$ | $N_{33\,4}L_{50\,5}E_{24\,4}M_{13\,4}B_{0\,3}$ | $N_{46\,9}L_{33\,2}E_{8\,3}M_{11\,2}B_{0\,4}$ | $N_{48\,7}L_{30\,5}E_{8\,6}M_{12\,1}B_{01}$ |
| | | ESR | — | — | 5 | 7 |
| | | Platelets | 25000 | 298000 | 202000 | 189000 |
| 10. | MN/30 | Hb gm % | 6.5 | 9.0 | | 9.8 |
| | | TLC | 8200 | 7300 | | 5600 |
| | | DLC | $N_{27}L_{48}E_1Abn_{24}$ | $N_{71}L_{23}M_6$ | | $N_{82}L_{17}M_1$ |
| | | ESR | — | — | | 60 |
| | | Platelets | 120000 | 230000 | | 150000 |

N-Neutrophils, L-Lymphocyte, E-Eosinophils, M-Monocyte, B-Basophil, Abn-Abnormal cell DETAILS OF LIVER, KIDNEY FUNCTION AND LIPID PROFILE OF THE PATIENTS TREATED FOR ACUTE PROMYELOCYTIC LEUKEMIA

| | | Pre Ayurvedic treatment | | | After 90 days of Ayurvedic treatment | | |
|---|---|---|---|---|---|---|---|
| S.no. | Name/Age | LFT | Lipid profile | KFT | LFT | Lipid profile | KFT |
| 1. | ARK/41 | NA | NA | NA | Bilirubin (T) - 1.2 mg/dl Bilirubin(D) - 0.3 mg/dl Protein total - 7.8 mg/dl | NA | Blood - 23 mgs/dl Serum - 0.8 mg/dl creatinine |

-continued

DETAILS OF LIVER, KIDNEY FUNCTION AND LIPID PROFILE OF THE PATIENTS TREATED FOR ACUTE PROMYELOCYTIC LEUKEMIA

| S.no. | Name/Age | Pre Ayurvedic treatment | | | After 90 days of Ayurvedic treatment | | |
|---|---|---|---|---|---|---|---|
| | | LFT | Lipid profile | KFT | LFT | Lipid profile | KFT |
| | | | | | SGOT - 29, SGPT - 35 Alk.P. - 161 | | |
| 2. | VR/40 | NA | NA | NA | NA | NA | NA |
| 3. | PK/50 | Bilirubin(T) - 04 mgs/100 ml Bilirubin(C) - 0.2 mgs/100 ml SGOT - 75 u/l, SGPT - 35 Alk.P. - 324 u/l | NA | Blood urea - 21 mgs/ 100 Serum creatinine - 1.1 mgs/ 100 ml | NA | NA | Blood - 34 mgs % serum creatinine - 1.3 mgs % |
| 4. | VC/48 | Bilirubin(T) - 0.7 mg % Bilirubin(C) - 0.3 mgs % Protein total - 7.0 gm % Albumin - 3.9 gm % Globulin - 3.1 gm % SGOT - 20 u/l, SGPT - 25 Alk.P. - 138 | Total cholestrol - 168 mg/dl HDL cholestrol - 380 mg/dl VLDL cholestrol - 29 mg/dl LDL cholestrol - 101 mg/dl Triglycerides - 433 mg/dl | Blood urea - 26 mg % Serum creatinine - 1.0 mg % Serum uric - acid 4.9 mg % | Bilirubin(T) - 0.72 mg/dl Bilirubin(D) - 0.3 mg/dl Protein total - 6.2 mg/dl Albumin - 3.6 SGOT - 20 u/l, SGPT - 25 Alk.P. - 430 | Cholestrol - 198 mg/dl | NA |
| 5. | F/29 | NA | NA | NA | NA | NA | NA |
| 6. | NS/15 | Bilirubin(T) - 0.5 mg/dl Bilirubin(D) - 0.3 mg/dl Protein total - 7.1 g/dl Albumin - 3.4 g/dl SGOT - 10 u/l, SGPT - 12 Alk.P. - 103 | Total cholestrol - 185 mg % HDL cholestrol - 42 mg % VLDL cholestrol - 21 mg % LDL cholestrol - 122 mg % Triglycerides - 105 mg % | Blood sugar - 90 mg % Blood urea - 19 mg % Serum creatinine - 0.8 mg % | NA | NA | NA |
| 7. | PR/48 | Bilirubin(T) - 1.57 mg/dl Bilirubin(D) - 0.14 mg/dl Bilirubin(ID) - 1.43 mg/dl Protein total - 6.9 mg/dl SGOT - 29, SGPT - 22 Alk.P. - 183.8 | NA | Blood - 34 mgs/ dl urea Serum - 1.2 mg/ dl creatinine Uric - 2.8 mg/ dl acid | Bilirubin(T) - 0.6 mg % Bilirubin(D) - 0.6 mg % Bilirubin(ID) - 0.5 mg % Protein total - 6.4 mg % Albumin - 3.7 mg % SGOT - 49 u/l, SGPT - 38 u/l, GGPT - 17 u/l Alk.P. - 17 u/l | Total cholestrol - 198 mg/dl HDL cholestrol - 49 mg % LDL cholestrol - 150 mg % VLDL cholestrol - 27 mg % Triglycerides - 136 mg % | Blood urea - 17 mg % Serum creatinine - 0.6 mg % Calcium - 9.7 mg % Phosphorus - 4.3 mg % Sodium - 114 meg/l Chloride - 107 meg/l |
| 8. | MS/28 | NA | NA | NA | Bilirubin(T) - 0.5 mg/dl Protein total - 6.6 g/dl Albumin - 4.2 g/dl SGOT - 62 u/l, SGPT - 138 u/l Alk.P. - 8 u/l | Total cholestrol - 146 mg/dl HDL cholestrol - 32 mg/dl LDL cholestrol - 53 mg/dl Triglyacerides - 306 mg/dl | Blood urea - 33 mg/dl Serum creatinine - 0.5 mg/dl |
| 9. | PS/29 | Bilirubin(T) - 0.4 mg/dl Bilirubin(D) - 0.2 mg/dl Bilirubin(ID) - 0.2 mg/dl Protein total - 7.6 g/dl Albumin - 4.4 g/dl SGOT - 126 u/l, SGPT - 49 u/l GGTP - 38 u/l Alk.P. - 217 u/l | Total cholestrol - 205 mg/dl HDL cholestrol - 31.25 mg/dl VLDL cholestrol - 26.99% LDL cholestrol - 118.42 mg/dl Triglycerides - 433 mg/dl | Blood urea - 45 mg/dl Serum creat- inine-0.90 mg/dl Calcium - 10.1 mg/dl Phosphorus - 4.1 mg/dl Sodium - 147 mEq/l Chloride - 103 mEq/l Potassium - 4.20 mEq/l | Bilirubin(T) - 0.7 mg/dl Bilirubin(D) - 0.2 mg/dl Bilirubin(ID) - 0.5 mg/dl Protein total - 7.7 g/dl Albumin - 4.6 g/dl SGOT - 253 u/l, SGPT - 365 u/l GGTP - 89 u/l Alk.P. - 473 u/l | Total cholestrol - 156 mg/dl HDL cholestrol - 22.15 mg % LDL cholestrol - 94.09 mg % VLDL cholestrol - 27.35 mg % Trigly- scerides - 187 mg/dl | Blood urea - 17 mg/dl Serum creatinine - 1.0 mg/d Calcium - 9.7 mg/dl Phosphorus - 2.9 mg/dl Sodium - 150 mE mEq/l Chloride - 105 mEq/l Potassium - 4.90 mEq/l |
| 10. | MN/30 | Bilirubin(T) - 1.7 mg/dl | Total cholestrol - 185 mg/dl | Blood urea - 46 mg/dl | Bilirubin(T) - 0.7 mg/dl | Total cholestrol - | Serum urea - 29.3 mg/dl |

-continued

DETAILS OF LIVER, KIDNEY FUNCTION AND LIPID PROFILE OF THE PATIENTS
TREATED FOR ACUTE PROMYELOCYTIC LEUKEMIA

| S.no. Name/Age | Pre Ayurvedic treatment | | | After 90 days of Ayurvedic treatment | | |
|---|---|---|---|---|---|---|
| | LFT | Lipid profile | KFT | LFT | Lipid profile | KFT |
| | Bilirubin(D) - 1.13 mg/dl<br>Bilirubin(ID) - 0.57 mg/dl<br>SGOT - 28 u/l,<br>SGPT - 35 u/l,<br>Alk.P. - 229 u/l | HDL cholestrol - 26 mg/dl<br>VLDL cholestrol - 93 mg/dl<br>LDL cholestrol 106 mg/dl<br>Triglyscerides - 506 mg/dl | Serum creatinine - 1.05 mg/dl<br>Calcium - 8.25 mg/dl | Bilirubin(D) - 0.3 mg/dl<br>SGOT - 22.8 iu/l<br>SGPT - 27.6 iu/l<br>Alk.P. - 360.5 iu/l | 136.8 mg/dl<br>HDL cholestrol - 46.2 mg/dl<br>LDL cholestrol - 56.5 mg/dl<br>VLDL cholestrol - 34.1 mg/dl | Serum creatinine - 1.0 mg/dl |

I claim:

1. A process for preparing an ayurvedic preparation, comprising the steps of:
    subjecting silver, mercury, sulphur and arsenic trisulphide to the steps of detoxification, grinding the detoxified mercury and silver in the presence of a citrus juice and then adding detoxified sulphur and again subjecting to the steps of grinding to obtain a greyish black powder, adding adding detoxified arsenic trisulfide thereto and subjecting to the step of grinding, imparting a shape such as a ball thereto, coating the ball with detoxified sulphur in the presence of a citrus juice and subjecting the coated ball to the step of slow firing, adding detoxified arsenic trisulphide and firing, repeating said steps of addition and firing ground in a citrus juice such that the weight of the ball is reduced by at least 10% to obtain an intermediate, adding serpentive and delphenium root thereto.

2. A process a claimed in claim 1 wherein the coated balls are introduced into an earthen vessel, sealed and then fired in the presence of cow dung.

3. A process as claimed in claim 1 wherein silver is detoxified by heating silver sheets to a red hot state, and then introducing into sesame oil, subjecting the sheets to repeated steps of heating and treatment with sesame oil.

4. A process as claimed in claim 3 wherein the sesame treated silver is subjected to repetitive steps of heating and then treating with butter milk.

5. A process as claimed in claim 4 wherein the butter milk treated silver is subjected to repetitive steps of heating and then treating with cow urine.

6. A process as claimed in claim 5 wherein the cow urine treated silver is then subjected to repetitive steps of heating and treatment in a herbal composition comprising amla, harar and bahera.

7. A process as claimed in claim 1 wherein the herbal treated silver is subjected to repetitive steps of heating and treatment with kulthi.

8. A process as claimed in claim 1 wherein the citrus juice is lemon juice.

9. The process as claimed in claim 3, wherein said repetitive steps comprise 7 repetitive steps.

10. A process as claimed in claim 1 wherein the step of detoxification of mercury comprises in preparing an amalgam of copper, mercury and a citrus juice, subjecting such an amalgam to repeated steps of distillation to obtain detoxified mercury.

11. A process as claimed in claim 1 wherein the step of detoxification of sulphur comprises in heating crystalline sulphur in the presence of melted butter, and then introducing into triffla to obtain a scum of pure sulphur which is then removed therefrom.

12. A process as claimed in claim 1 wherein the step of detoxification of arsenic trisulphide comprises in wrapping arsenic trisulphide in cotton cloth and then introduced in a vessel of calcium oxide solution and into another vessel of pumpkin juice and boiled each time for a period of 3 to 5 hours.

13. A process as claimed in claim 1 wherein one part of detoxified silver is ground with one part of detoxified mercury in a citrus juice and that one part of detoxified sulphur is then added thereto obtain a greyish black powder.

14. A process as claimed in claim 12 wherein one part of arsenic trisulphide ground in a citrus juice is added to the greyish black powder and made into a shape.

15. The process as claimed in claim 14, wherein one part of detoxified sulphur is ground in citrus juice and coated to said shape and then introduced in said vessel and fired in cowdung.

16. A process as claimed in claim 1 wherein vessel containing said fired mixture is opened and further arsenic trisulphide ground in the presence of lemon juice is added, the vessel closed and again fired and subjected to repeated steps to obtain a potent preparation.

* * * * *